May 25, 1976 W. E. LAMMERTS Plant Pat. 3,893
LILAC PLANT
Filed March 24, 1975
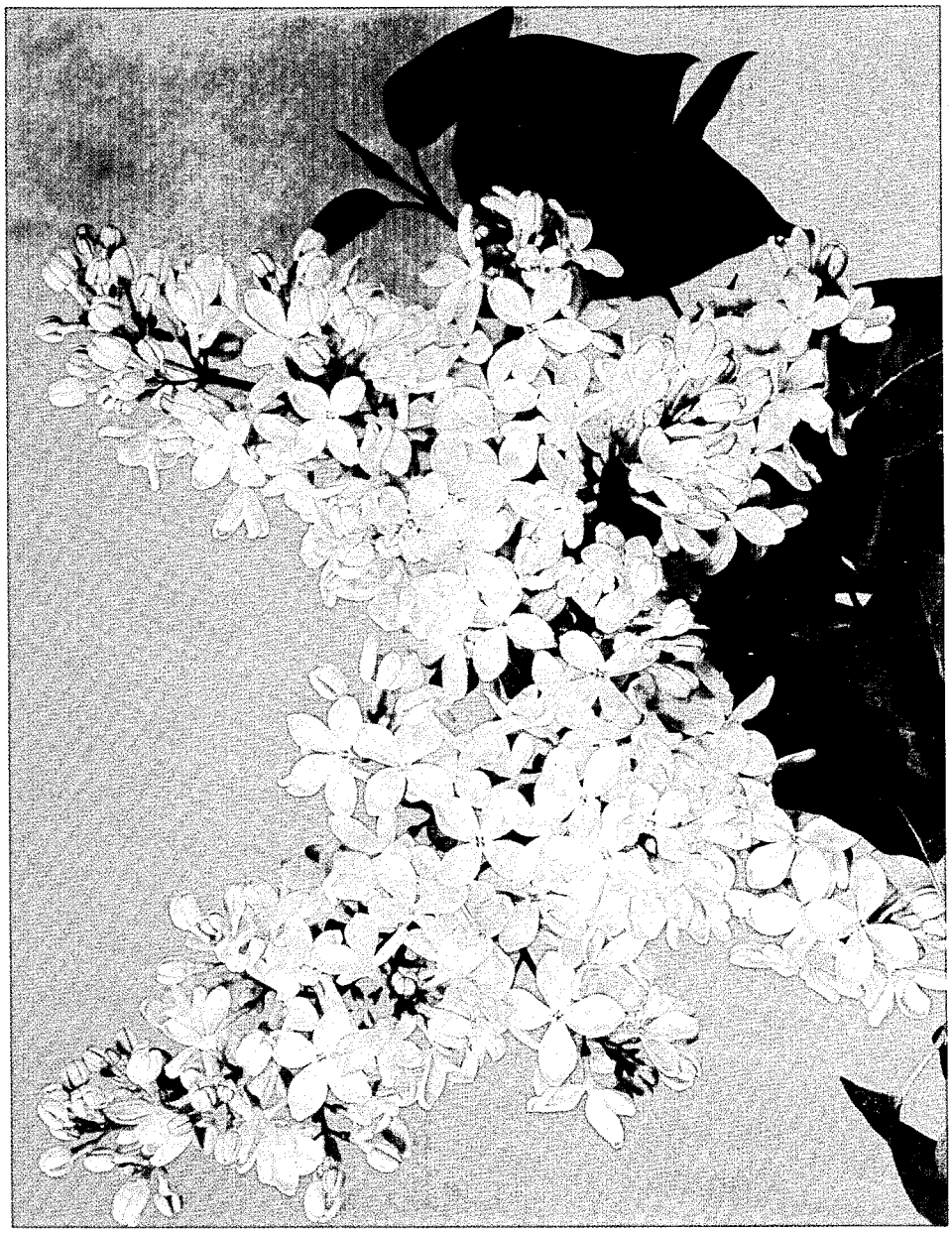

United States Patent

Plant Pat. 3,893

Patented May 25, 1976

3,893

LILAC PLANT

Walter E. Lammerts, Corralitos, Calif., assignor to Hines Wholesale Nurseries, Santa Ana, Calif.

Filed Mar. 24, 1975, Ser. No. 561,328

Int. Cl. A01h *5/00*

U.S. Cl. Plt.—66 1 Claim

The present invention relates to a new and distinct variety of lilac plant originated by me by crossing two unnamed and unpatented seedlings, each of which was derived from seedlings derived from various crosses I have made with seed of an unnamed and unpatented early-leafing variety identified by me in my breeding records by the identification number C112.

The primary objective in making this cross was to further and improve the objectives set forth in Plant Pat. 1,238, previously granted to me on Jan. 5, 1954. As set forth in this prior application, I had produced a lilac which would flower normally in Southern California and comparable climatic areas having short and mild winters. The present invention relates to a lilac plant which requires less than normal winter-chilling required by most lilacs, including the usual eastern lilacs, and still produces normal flowering bloom clusters.

My new variety is characterized by its ability to achieve normal flowering without requiring normal winter-chilling; by its regularity and abundance of bloom consisting of very large flower clusters measuring from 7 to 10 inches in length and from 7 to 12 inches in width; and by the size of relatively large florets, at times measuring from ⅞ of an inch to 1 3/16 inches in diameter. Occasional flower clusters will be as large as 12 inches in both length and width.

The new variety was asexually reproduced by me on cultivated property known as Descanso Distributors Inc. at Chino, Calif. Reproduction of this new variety was made by cuttings and also by budding to Ligustrum understock, and as a result established that the foregoing distinguishing characteristics come true to form and are established and transmitted through succeeding propagations.

The drawing which accompanies this petition shows a typical view of the flowers and foliage of my new lilac variety and is portrayed in color as fairly as can possibly be obtained by this method of illustration.

To facilitate identification of the important colors, I have used the color terminology of the R.H.S. Colour Chart issued by the Royal Horticultural Society of London.

Locality where grown and observed: Descanso Distributors, Inc. Nursery in Chino, Calif.

Parentage: Seedling resulting from planned propagation.

Seed parent.—A large-petalled unpatented seedling of an unnamed early-leafing variety identified by me in my breeding records as C112, crossed to an unnamed seedling identified in my breeding records as 42–108–3.

Pollen parent.—A deep pink unnamed seedling derived from from seed produced by open pollenation of a seedling of an unpatented variety named Syringa "Buffon", identified in my breeding records as 42–109–4.

The seeds which were produced by this cross in 1950, were sown in 1951, and plants first bloomed in 1953.

Blooming habit: Early; usually from about the early part of March to mid-April in Southern California. In full flower and leaf by the end of March.

*The plant*

Form of plant: Bush.

Growth: Upright; vigorous, compact.

Branches:

New growth is in the Yellow-Green Group, Plates 144B to 144C.

Mature growth is in the Greyed-Green Group, Plate 197C to Plate 197D.

Foliage:

Size.—2 inches to 2½ inches wide and from about 2¾ inches to 3½ inches long.

Quantity.—Abundant.

Shape.—Ovate with an acuminate tip, and a cordate base. The leaf margin is entire.

Venation.—Pinnate.

Arrangement.—Opposite.

Color.—New leaves—In the Yellow-Green Group, Plates 144A to 144B.

Mature leaves.—In the Green Group, Plates 139B to 139C.

*The flower*

Bud:

Individual florets of cluster.

Size.—Large.

Form.—Stubby; rounded tip.

Color.—In the Red-Purple Group, Plates 70C to 70D, fading to Red-Purple Group, Plate 70C at the tip.

Bloom: Individual florets of cluster, about 7/16 of an inch, to about ½ inch in diameter. Florets are borne in large clusters measuring from 7 to 10 inches in length and from 7 to 12 inches in width, with occasional clusters as large as 12 inches in both length and width. Individual raceme length comprising the cluster range from 2 inches to 2¼ inches in length.

Color.—Center of the open flower starts at Purple Group, Plate 78C on the edge to Purple Group, Plate 78D towards the center.

Open flowers fade towards the tips from Red-Purple Group, Plate 65D to almost White Group, Plate 155B at the base. Underside of the flowers is in Purple Group, Plates 75A to 75B.

I claim:

1. A new and distinct variety of lilac plant, substantially as herein shown and described, characterized particularly as to novelty by its relatively short and mild winter-chilling requirements, by its regular and abundant production of large flower clusters consisting of large individual florets, by its vigorous habit of plant growth, and by its abundant production of large and attractive foliage.

No references cited.

ROBERT E. BAGWILL, Primary Examiner